United States Patent
Racenet et al.

(10) Patent No.: US 8,757,467 B2
(45) Date of Patent: Jun. 24, 2014

(54) SURGICAL INSTRUMENT WITH SEQUENTIAL CLAMPING AND CUTTING

(75) Inventors: Danyel Racenet, Middletown, CT (US); David M. Farascioni, Bethel, CT (US); Dino Kasvikis, Middletown, CT (US); Katelyn O'Donnell, East Haven, CT (US)

(73) Assignee: Covidien LP, Mansfield, MA (US)

( * ) Notice: Subject to any disclaimer, the term of this patent is extended or adjusted under 35 U.S.C. 154(b) by 120 days.

(21) Appl. No.: 12/868,218

(22) Filed: Aug. 25, 2010

(65) Prior Publication Data

US 2011/0068147 A1 Mar. 24, 2011

Related U.S. Application Data

(63) Continuation of application No. 12/724,699, filed on Mar. 16, 2010, now abandoned, which is a continuation of application No. 12/575,098, filed on Oct. 7, 2009, now abandoned, which is a continuation of application No. 12/430,219, filed on Apr. 27, 2009, now abandoned.

(60) Provisional application No. 61/050,272, filed on May 5, 2008.

(51) Int. Cl.
*A61B 17/10* (2006.01)
*A61B 17/04* (2006.01)

(52) U.S. Cl.
USPC ........................................... 227/180.1

(58) Field of Classification Search
CPC ........... A61B 2017/07214; A61B 2017/00473; A61B 2017/320072; A61B 17/0487
USPC ............... 227/175.1–182.1, 19; 81/339, 340; 606/219–220; 74/575, 578
See application file for complete search history.

(56) References Cited

U.S. PATENT DOCUMENTS

| 3,080,564 A | 3/1963 | Strekopitov et al. |
| 3,269,630 A | 8/1966 | Fleischer |

(Continued)

FOREIGN PATENT DOCUMENTS

| EP | 0 246 870 A2 | 11/1987 |
| EP | 1 550 412 A2 | 7/2005 |

(Continued)

OTHER PUBLICATIONS

European Search Report for corresponding EP 10 25 0934, date of completion is Aug. 19, 2010 (3 pages).

(Continued)

*Primary Examiner* — Robert Long

(57) ABSTRACT

A surgical fastening instrument including a handle portion, an elongated portion, an end effector and a clamp is disclosed. The elongated portion extends distally from the handle portion. The end effector includes a pair of jaws having a tissue contacting surface disposed substantially transverse to the longitudinal axis of the elongated portion. The end effector is disposed adjacent a distal end of the elongated portion, and at least one of the jaw members is movable with respect to the other between an open position and an approximated position for engaging body tissue therebetween. The clamp has a clamping surface extending substantially transversely from an elongated member and has a height exceeding a height of the elongated member to extend adjacent a side surface of the jaw containing the plurality of fasteners. The clamp is movable from a proximal position to a distal position for engaging body tissue.

20 Claims, 20 Drawing Sheets

(56) References Cited

U.S. PATENT DOCUMENTS

| | | | |
|---|---|---|---|
| 3,315,863 A | 4/1967 | O'Dea | |
| 3,589,589 A * | 6/1971 | Akopov | 227/153 |
| 3,692,224 A * | 9/1972 | Astafiev et al. | 227/19 |
| 3,889,683 A * | 6/1975 | Kapitanov et al. | 606/143 |
| 4,216,891 A | 8/1980 | Behlke | |
| 4,344,420 A | 8/1982 | Forder | |
| 4,354,628 A | 10/1982 | Green | |
| 4,383,634 A * | 5/1983 | Green | 227/19 |
| 4,506,671 A | 3/1985 | Green | |
| 4,508,253 A | 4/1985 | Green | |
| 4,530,453 A | 7/1985 | Green | |
| 4,566,620 A | 1/1986 | Green et al. | |
| 4,568,009 A | 2/1986 | Green | |
| 4,589,582 A | 5/1986 | Bilotti | |
| 4,617,928 A | 10/1986 | Alfranca | |
| 4,665,916 A | 5/1987 | Green | |
| 4,684,051 A | 8/1987 | Akopov et al. | |
| 4,715,520 A * | 12/1987 | Roehr et al. | 227/19 |
| 4,788,978 A | 12/1988 | Strekopytov et al. | |
| 4,802,614 A * | 2/1989 | Green et al. | 227/19 |
| 4,819,853 A | 4/1989 | Green | |
| 4,834,112 A * | 5/1989 | Machek et al. | 600/587 |
| 4,869,414 A | 9/1989 | Green et al. | |
| 4,881,545 A | 11/1989 | Isaacs et al. | |
| 4,915,100 A | 4/1990 | Green | |
| 5,071,052 A * | 12/1991 | Rodak et al. | 227/175.2 |
| 5,100,042 A * | 3/1992 | Gravener et al. | 227/176.1 |
| 5,242,457 A | 9/1993 | Akopov et al. | |
| 5,344,060 A * | 9/1994 | Gravener et al. | 227/180.1 |
| 5,389,098 A | 2/1995 | Tsuruta et al. | |
| 5,392,979 A * | 2/1995 | Green et al. | 227/179.1 |
| 5,405,073 A | 4/1995 | Porter | |
| 5,452,836 A | 9/1995 | Huitema et al. | |
| 5,454,824 A * | 10/1995 | Fontayne et al. | 606/151 |
| 5,465,894 A | 11/1995 | Clark et al. | |
| 5,509,596 A * | 4/1996 | Green et al. | 227/176.1 |
| 5,547,117 A | 8/1996 | Hamblin et al. | |
| 5,558,266 A * | 9/1996 | Green et al. | 227/178.1 |
| 5,579,978 A * | 12/1996 | Green et al. | 227/175.3 |
| 5,607,094 A | 3/1997 | Clark et al. | |
| 5,632,432 A * | 5/1997 | Schulze et al. | 227/176.1 |
| 5,653,373 A | 8/1997 | Green et al. | |
| 5,662,260 A | 9/1997 | Yoon | |
| 5,692,668 A * | 12/1997 | Schulze et al. | 227/175.1 |
| 5,706,997 A * | 1/1998 | Green et al. | 227/175.2 |
| 5,706,998 A * | 1/1998 | Plyley et al. | 227/175.3 |
| 5,810,240 A * | 9/1998 | Robertson | 227/175.2 |
| 5,928,264 A | 7/1999 | Sugarbaker et al. | |
| 6,053,908 A * | 4/2000 | Crainich et al. | 606/1 |
| 6,398,795 B1 | 6/2002 | McAlister et al. | |
| 6,805,273 B2 | 10/2004 | Bilotti et al. | |
| 6,988,650 B2 | 1/2006 | Schwemberger et al. | |
| 7,147,139 B2 | 12/2006 | Schwemberger et al. | |
| 7,204,404 B2 | 4/2007 | Nguyen et al. | |
| 7,207,472 B2 | 4/2007 | Wukusick et al. | |
| 7,278,563 B1 | 10/2007 | Green | |
| 7,374,566 B1 * | 5/2008 | Schossau | 606/167 |
| 7,401,721 B2 | 7/2008 | Holsten et al. | |
| 7,472,814 B2 | 1/2009 | Mastri et al. | |
| 7,543,730 B1 | 6/2009 | Marczyk | |
| 7,810,690 B2 | 10/2010 | Bilotti et al. | |
| 2002/0065523 A1 | 5/2002 | McAlister et al. | |
| 2005/0139636 A1 | 6/2005 | Schwemberger et al. | |
| 2005/0145672 A1 | 7/2005 | Schwemberger et al. | |
| 2005/0247753 A1 | 11/2005 | Kelly et al. | |
| 2005/0263563 A1 * | 12/2005 | Racenet et al. | 227/176.1 |
| 2006/0163312 A1 * | 7/2006 | Viola et al. | 227/175.1 |
| 2007/0039996 A1 * | 2/2007 | Mather et al. | 227/176.1 |
| 2007/0039997 A1 * | 2/2007 | Mather et al. | 227/176.1 |
| 2007/0095877 A1 * | 5/2007 | Racenet et al. | 227/175.2 |
| 2007/0187456 A1 * | 8/2007 | Viola et al. | 227/175.1 |
| 2008/0078800 A1 | 4/2008 | Hess et al. | |
| 2009/0302093 A1 * | 12/2009 | Kasvikis | 227/180.1 |
| 2010/0048988 A1 | 2/2010 | Pastorelli et al. | |
| 2010/0081883 A1 * | 4/2010 | Murray et al. | 600/204 |
| 2010/0133320 A1 | 6/2010 | Bilotti et al. | |
| 2012/0071897 A1 * | 3/2012 | Kasvikis | 606/139 |
| 2013/0140343 A1 * | 6/2013 | Knodel | 227/180.1 |

FOREIGN PATENT DOCUMENTS

| | | |
|---|---|---|
| EP | 1621139 A | 2/2006 |
| EP | 1 875 868 A1 | 1/2008 |
| EP | 1908414 A | 4/2008 |
| EP | 1 935 354 A2 | 6/2008 |
| EP | 1 550 411 B1 | 7/2009 |
| EP | 2 130 501 A1 | 12/2009 |
| GB | 2029754 | 3/1980 |
| WO | 02/30296 | 4/2002 |
| WO | 2006/055385 | 5/2006 |

OTHER PUBLICATIONS

European Search Report EP 09251240 dated Oct. 5, 2009. (8 pages).
European Search Report for EP 09252246.5-1269 date of completion is Nov. 24, 2009 (3 pages).
European Search Report for corresponding EP09251250, date of mailing is Aug. 16, 2012 (12 pgs).
European Search Report dated Oct. 17, 2013 in European Application No. 13184619.

* cited by examiner

SURGICAL INSTRUMENT WITH SEQUENTIAL CLAMPING AND CUTTING

CROSS REFERENCE TO RELATED APPLICATIONS

This application is a Continuation of, claims the benefits of and priority to U.S. patent application Ser. No. 12/724,699 filed on Mar. 16, 2010 now abandoned which is a Continuation of, claims the benefits of and priority to U.S. patent application Ser. No. 12/575,098 filed on Oct. 7, 2009, now abandoned which is a Continuation of, claims the benefits of and priority to U.S. patent application Ser. No. 12/430,219 filed on Apr. 27, 2009, now abandoned which claims the benefits of and priority to U.S. Provisional Application No. 61/050,272, filed on May 5, 2008, the entire contents of each of which are incorporated herein by reference.

BACKGROUND

1. Technical Field

The present disclosure relates generally to a surgical instrument and, more specifically, to a surgical instrument for clamping tissue, approximating anvil and cartridge assemblies, and for surgically joining tissue.

2. Background of Related Art

Surgical stapling instruments used for applying parallel rows of staples through compressed living tissue are well known in the art, and are commonly used, for example, for closure of tissue or organs prior to transection, prior to resection, in anastomoses, and for occlusion of organs in thoracic and abdominal procedures.

Typically, such surgical stapling instruments include an anvil assembly, a cartridge assembly for supporting an array of surgical staples, an approximation mechanism for approximating the cartridge and anvil assemblies, an alignment or guide pin assembly for capturing tissue between the cartridge and anvil assemblies and for maintaining alignment between the cartridge and anvil assemblies during approximation and firing, and a firing mechanism for ejecting the surgical staples from the cartridge assembly.

In use, a surgeon approximates the anvil and cartridge members and then fires the instrument to emplace staples in tissue. Additionally, the surgeon may use the same instrument or a separate instrument to cut the tissue adjacent, across or between the row(s) of staples.

SUMMARY

The present disclosure relates in one aspect to a surgical instrument including a handle portion, an elongated portion, a pair of jaw members and a clamp. The elongated portion extends distally from the handle portion. The pair of jaw members are disposed adjacent a distal end of the elongated portion, and at least one of the jaw members is movable with respect to the other jaw member in a distal direction between an open position and an approximated position for engaging body tissue therebetween. One of the jaw members includes a plurality of rows of fasteners positioned substantially transverse to a longitudinal axis of the elongated portion and arranged in substantially linear rows. The clamp has a clamping surface extending substantially transversely from an elongated member and having a height exceeding a height of the elongated member to extend adjacent a side surface of the jaw containing the plurality of fasteners. The clamp is movable from a proximal position to a distal position for engaging body tissue. A tissue-contacting surface of each of the jaw members is disposed substantially transverse to the longitudinal axis of the elongated portion.

Preferably, the clamp is independently movable with respect to the jaw members. Alternatively, the clamp can be moved automatically with approximation of the jaws.

The surgical instrument can include in some embodiments a knife movable between a proximal and distal position. Various configurations of the knife are disclosed including a knife that includes at least one of a longitudinally tapered tissue-contacting surface, and a tissue-contacting surface having a raised middle portion with respect to its side portions.

In alternate embodiments, the elongated portion can include at least one of a curved portion, a bend or an angle.

An embodiment of the present disclosure includes at least one of the jaw members (e.g. a cartridge assembly and/or an anvil assembly) configured to be removable from the instrument. The cartridge assembly can include two (or more) rows of staples with a knife disposed between them. In another embodiment, the cartridge assembly can include first and second rows of staples with the first row of staples disposed between a knife and the second row of staples. That is, the knife could be on one side of two or more rows of staples.

The present disclosure in another aspect relates to a surgical stapling instrument including a handle portion, an elongated portion, an end effector and a knife. The elongated portion extends distally from the handle portion and defines a first longitudinal axis. The end effector includes a cartridge assembly and an anvil assembly, and is disposed adjacent a distal end of the elongated portion. A tissue contacting surface of the cartridge and anvil assemblies is disposed substantially transverse to a longitudinal axis of the elongated portion. At least one of the cartridge assembly and the anvil assembly is movable with respect to the other from an open position to an approximated position for engaging body tissue therebetween. The cartridge assembly is configured to house a plurality of staples. The knife is movable from a proximal to a distal position. The knife includes at least one of a longitudinally tapered tissue-contacting surface and a raised middle portion.

The present disclosure in another aspect relates to a method of performing a lower anterior resection. The method includes the step of providing a surgical fastening instrument including a handle portion, an elongated portion, a pair of jaw members and a clamp. The elongated portion extends distally from the handle portion. The pair of jaw members is disposed adjacent a distal portion of the elongated portion. A tissue-contacting surface of each of the jaw members is disposed substantially transverse to the longitudinal axis of the elongated portion. The clamp is disposed adjacent at least one jaw member and having a tissue clamping surface extending substantially transversely from an elongated member and having a height exceeding the height of the elongated member. The method also includes the steps of moving the clamp from a proximal position towards a distal position to engage intestinal tissue, cleaning the interior of the intestinal tissue, moving at least one of the jaw members with respect to the other from an open position to an approximated position to engage intestinal tissue adjacent the intestinal tissue engaged by the clamp, and advancing a plurality of fasteners into the tissue in a direction substantially parallel to the longitudinal axis of the elongated portion.

The method may include the step of cutting intestinal tissue adjacent the joined intestinal tissue. In some embodiments, the clamp is independently movable with respect to the jaw members.

A knife can be disposed in mechanical engagement with at least one jaw member. Various configurations of the knife are disclosed including a knife that has at least one of a longitudinally tapered tissue-contacting surface, and a tissue-contacting surface having a raised middle portion with respect to its side portions.

The method of providing an instrument can include providing a surgical instrument having a cartridge assembly and an anvil assembly, wherein the cartridge assembly includes two (or more) rows of staples and a knife disposed between the two rows of staples, or on one side of two or more rows of staples.

BRIEF DESCRIPTION OF FIGURES

Various embodiments of the presently disclosed surgical stapling instrument are disclosed herein with reference to the drawings, wherein:

FIGS. 12-15 illustrate the handle portion of the surgical stapling instrument according to one embodiment of the present disclosure shown at different stages of operation, wherein FIG. 12 shows a first movable handle in an open position and a second movable handle in an open position, FIG. 13 shows the first movable handle in a partially actuated position, FIG. 14 shows the first movable handle in a partially actuated position and the second movable handle in an actuated position; and FIG. 15 shows the first movable handle in an actuated position and the second movable handle in an actuated position;

DETAILED DESCRIPTION

Figure 1:
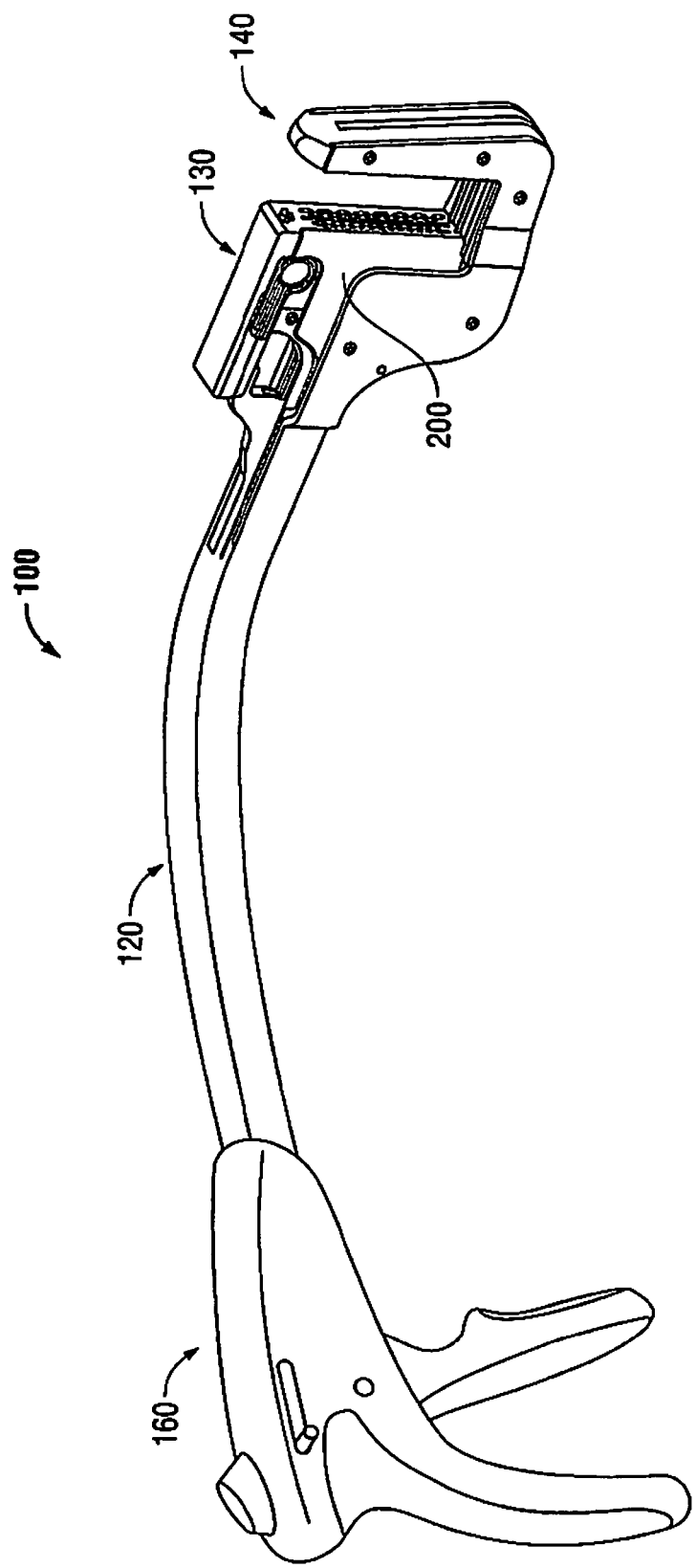
FIG. 1 illustrates an embodiment of the surgical stapling instrument of the present disclosure including a curved elongated portion.

Embodiments of the presently disclosed surgical fastening instrument are described in detail with reference to the drawings, wherein like reference numerals designate corresponding elements in each of the several views. In the drawings and the description that follows, the term "proximal" refers to the end of the surgical stapling instrument that is closer to the operator, whereas the term "distal" refers to the end of the surgical stapling instrument that is further from the operator. It should be appreciated that the instrument described and illustrated herein is configured to fire surgical staples against an anvil surface; however, it can also be used to fire other forms of staples, fasteners, clips, as well as two part fasteners, made of metallic or polymeric material.

The surgical stapling instrument of a first embodiment of the present disclosure is indicated as reference numeral 100 in the accompanying figures. Details of an angled surgical stapler are disclosed in commonly-owned U.S. Patent Application Serial No. 2007/0187456 filed on Apr. 10, 2007, the entire contents of which are incorporated by reference herein.

Surgical stapling instrument 100 is configured for clamping tissue, approximating its jaw members, emplacing staples or fasteners in tissue, and cutting tissue. Generally, with reference to FIG. 1, surgical stapling instrument 100 includes a handle portion 160, an elongated portion 120 and a pair of jaw members which includes a cartridge assembly 130 and an anvil assembly 140, both extending substantially transverse to a longitudinal axis of the instrument.

Surgical stapling instrument 100 also includes a clamp 200, disposed adjacent cartridge assembly 130, for instance. Upon activation of clamp 200 (discussed in detail below), clamp 200 is translated distally to compress tissue (e.g., an organ), thus temporarily occluding the organ. In disclosed embodiments, the tissue is compressed between clamp 200 and a portion of the jaw member housing anvil assembly 140. Additionally, distal translation of clamp 200 allows the user to help ascertain where the staples will be emplaced.

After clamp 200 has been advanced and the organ is occluded, the user may then approximate the jaw members about the organ. Subsequently, staples 300 may be fired (e.g., simultaneously or sequentially) from staple cartridge 130 in a direction substantially parallel to the longitudinal axis of the instrument and emplaced in the organ held by clamp 200 and between jaw members. Further, the user may then transect or cut the stapled organ with a knife 220. The knife can be built into the instrument or the surgeon can utilize a separate knife. In various embodiments, the cutting may be done substantially simultaneously as stapling the organ. Additionally, the use of at least one guide pin 250 may be used to help facilitate alignment between cartridge assembly 130 and anvil assembly 140.

Figure 2A:
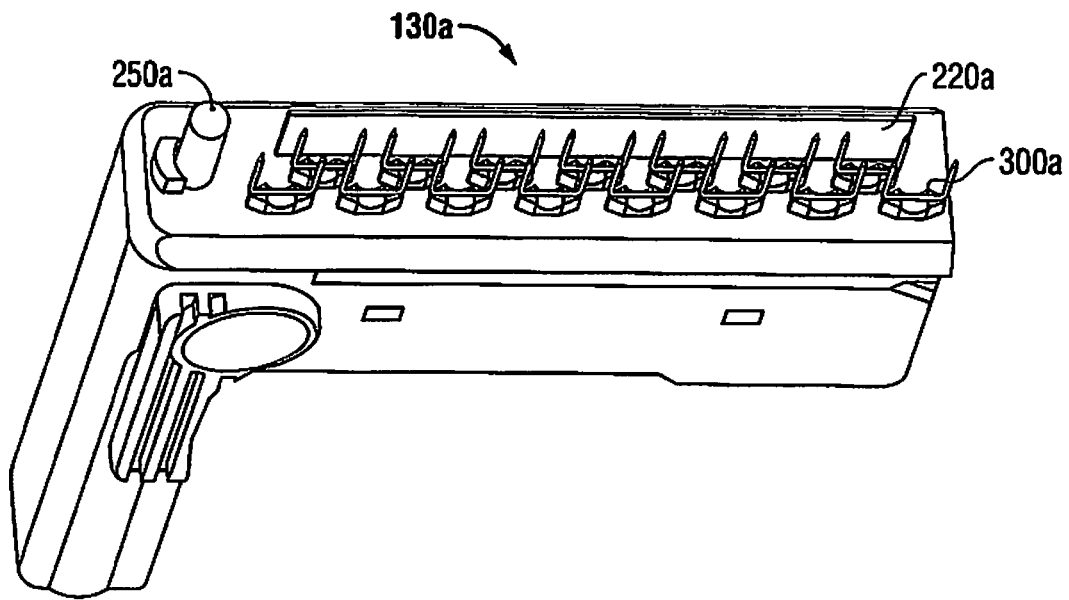
FIGS. 2a and 2b illustrate two embodiments of a cartridge assembly for use with the surgical stapling instrument.
Figure 2B:
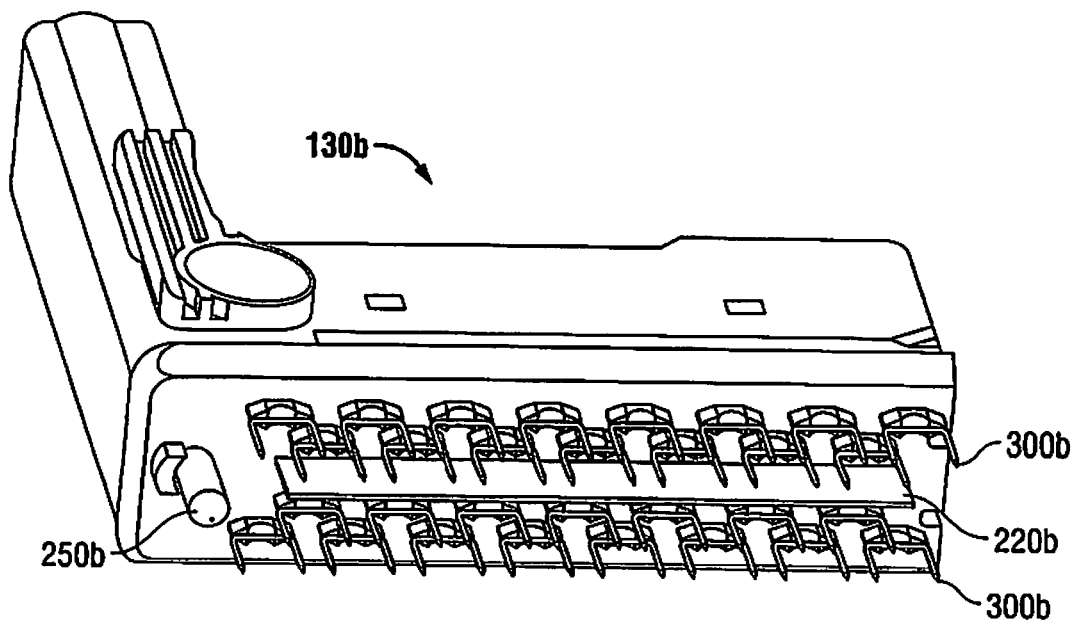

With reference to FIGS. 2A and 2B, two different embodiments of a portion of surgical instrument 100 having a cartridge are shown. Cartridge assembly 130a of FIG. 2A and cartridge assembly 130b of FIG. 2B are respectively shown having different locations of knife 220a, 220b. Specifically, FIG. 2a illustrates knife 220a adjacent one of the two rows of staples of fasteners 300a. That is, one row of staples is positioned between the knife 220b and the other row of staples. FIG. 2b shows knife 220b between two rows of staples or fasteners 300b (the cartridge having two pairs of rows of staples). As can be appreciated, the knife can be positioned adjacent the two or more rows of staples or positioned between the two or more rows of staples.

As shown, the rows of staples are arranged in a substantially linear configuration and arranged in rows substantially transverse to a longitudinal axis of the instrument. While guide pin 250a is shown in a particular location in FIG. 2a, it is envisioned that guide pin 250a and knife 220a could be positioned relatively closer to one another, such that at least a portion of the row of staples 300a and/or knife 220a extends beyond guide pin 250a. An example of when a knife 220a could extend beyond guide pin 250a is when knife 220a and guide pin 250a are not aligned. Similarly, with regard to FIG. 2b, it is envisioned that guide pin 250b and knife 220b could be positioned relatively closer to one another, such that at least a portion of the row of staples 300b and/or knife 220b extends beyond guide pin 250b. The guide pin 250 could also be semicircular in cross section so it is flat on one side to provide space for the knife to pass by in embodiments where the knife extends to or beyond the guide pin.

With reference to FIGS. 3-6, the jaw members 130c, 140c and clamp 200c are shown. Specifically, in FIG. 3, the orientation of clamp 200c and the jaw members 130c, 140c is most visible. As shown, clamp 200c includes an elongated tissue-contacting surface 202c and, in its proximal position, is located adjacent cartridge assembly 130c. Tissue contacting surface 202c extends substantially transverse to a longitudinal axis of the instrument and in the illustrated embodiment, has a length similar to a length of the anvil assembly.

In the illustrated embodiment, the length of the clamping surface (i.e., tissue contacting surface 202c) exceeds the length of the staple line and/or knife slot and exceeds the height of the elongated member from which it substantially transversely extends. In this manner, the clamp 200c slides alongside, but spaced from, a side surface of the jaw member 130c. It is envisioned that tissue-contacting surface 202c of clamp 200c could be smooth, jagged, serrated (e.g., to interlock with tissue), rounded, flat, angled, beveled, bent (to provide a greater surface area), etc., or any combination thereof. It is further envisioned that a portion of the end effector (e.g., part of anvil 140c or adjacent thereto) could include a groove (not explicitly shown in FIGS. 3-6) for accepting clamp 200c to help secure tissue therebetween.

In a contemplated embodiment, clamp 200c extends from a distal portion of the elongated member, which extends through the elongated portion of the surgical instrument. A proximal portion of the elongated member is disposed in mechanical cooperation with a movable portion (e.g., "clamp handle" which is a movable handle, screw, etc.) of the handle assembly. In such an embodiment, for example, actuation of the movable handle causes the elongated member to translate distally within the elongated portion, which causes enlarged clamp head 200c to travel distally to compress tissue. Additionally, a second elongated member may extend through the elongated portion of the instrument and be used to fire staples from the cartridge assembly 130c. The second elongated member may be proximally engaged with a movable portion (e.g., "firing handle" which is the same as the clamp handle or a different movable portion) of the handle assembly and may be distally engaged with a portion of the cartridge assembly 130c. Here, actuation of the firing handle may cause distal translation of the second elongated member, which may cause approximation of the jaw members and/or staples to be fired from cartridge assembly 130c.

Figure 3:
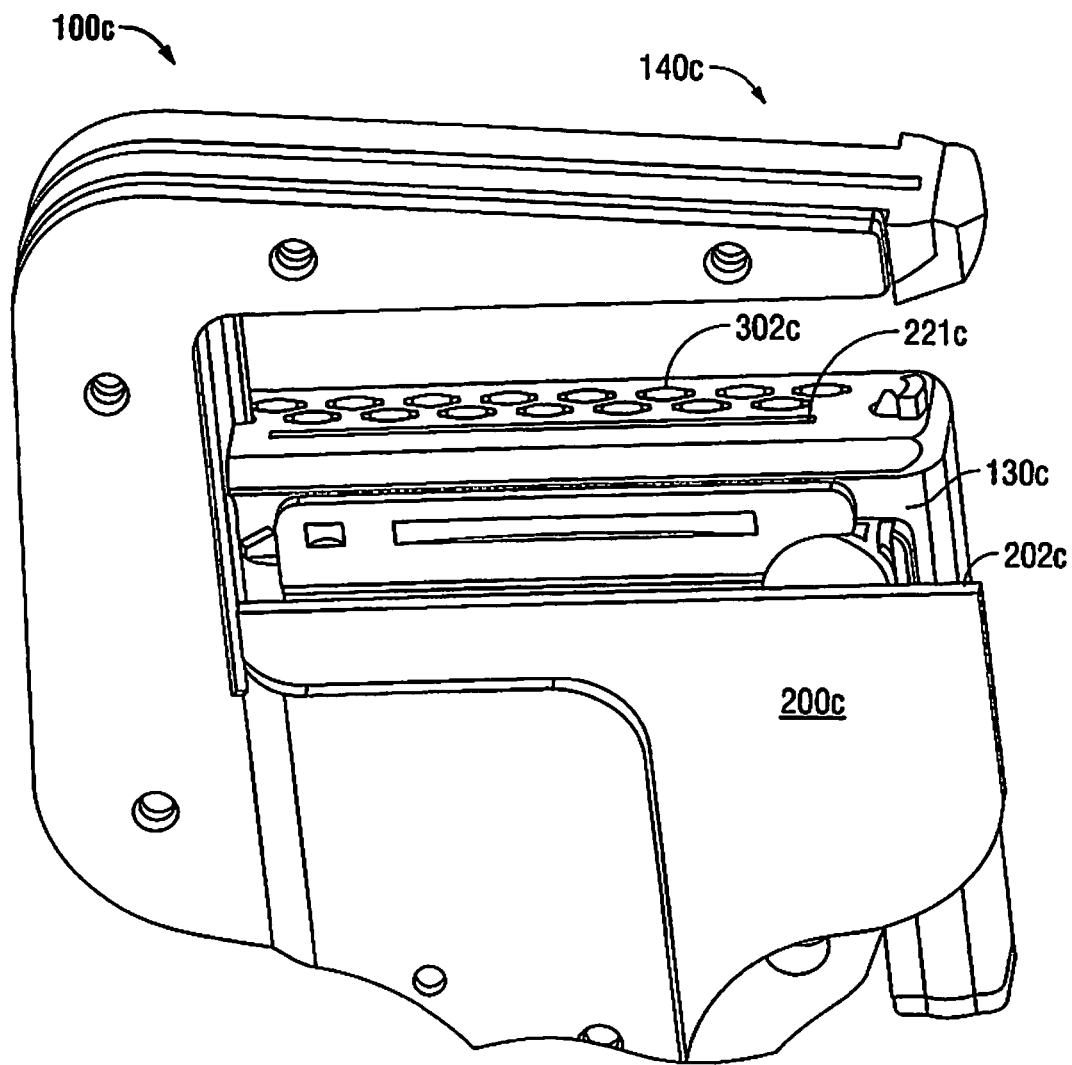
FIGS. 3 and 4 illustrate enlarged opposite side perspective views of the distal portion of the instrument of FIG. 1 showing the clamp and cartridge in a proximal (retracted) position for use with the surgical stapling instrument.
Figure 4:
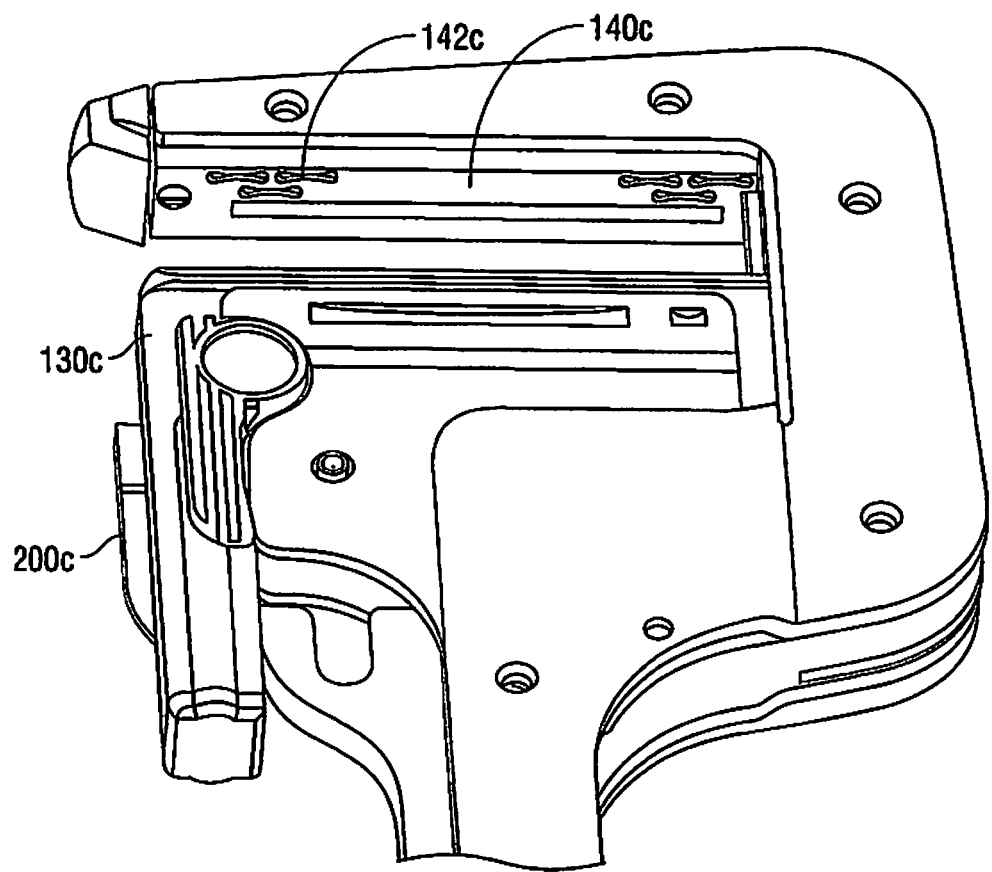
Figure 5:
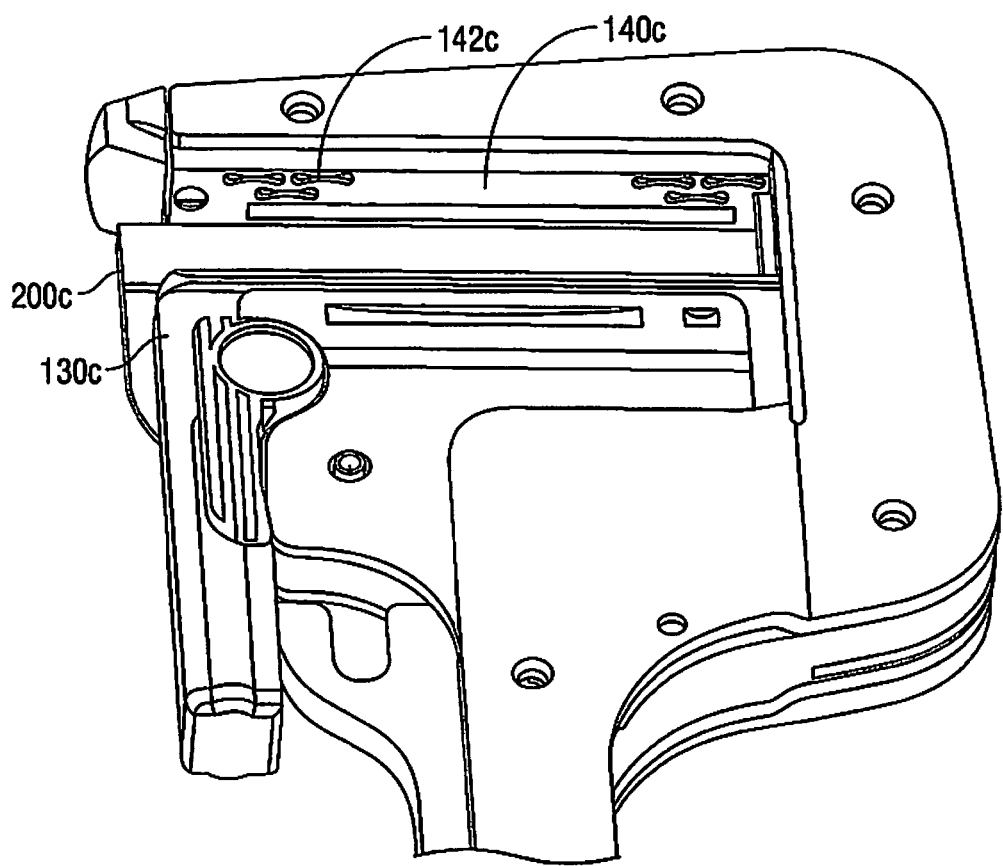
FIG. 5 is a perspective view similar to FIG. 4 showing the clamp in a distal position and the cartridge in a proximal position.
Figure 6:
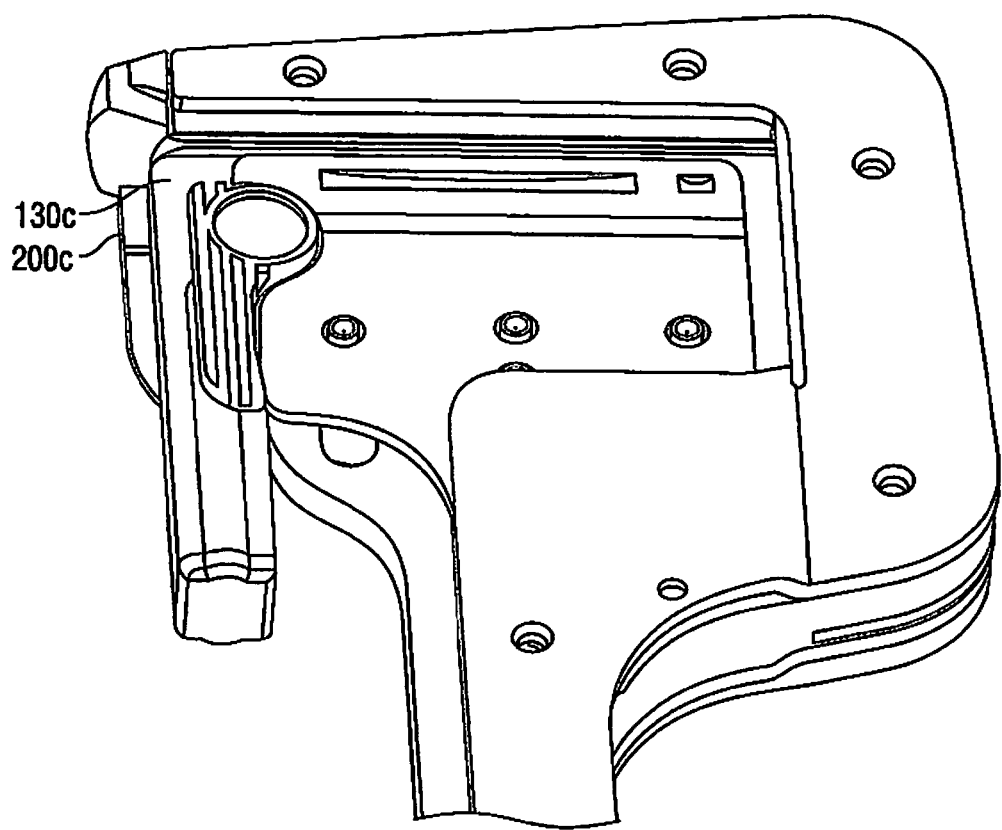
FIG. 6 is a perspective view similar to FIG. 5 showing the clamp in a distal position and the cartridge in a distal position.
Figure 7:
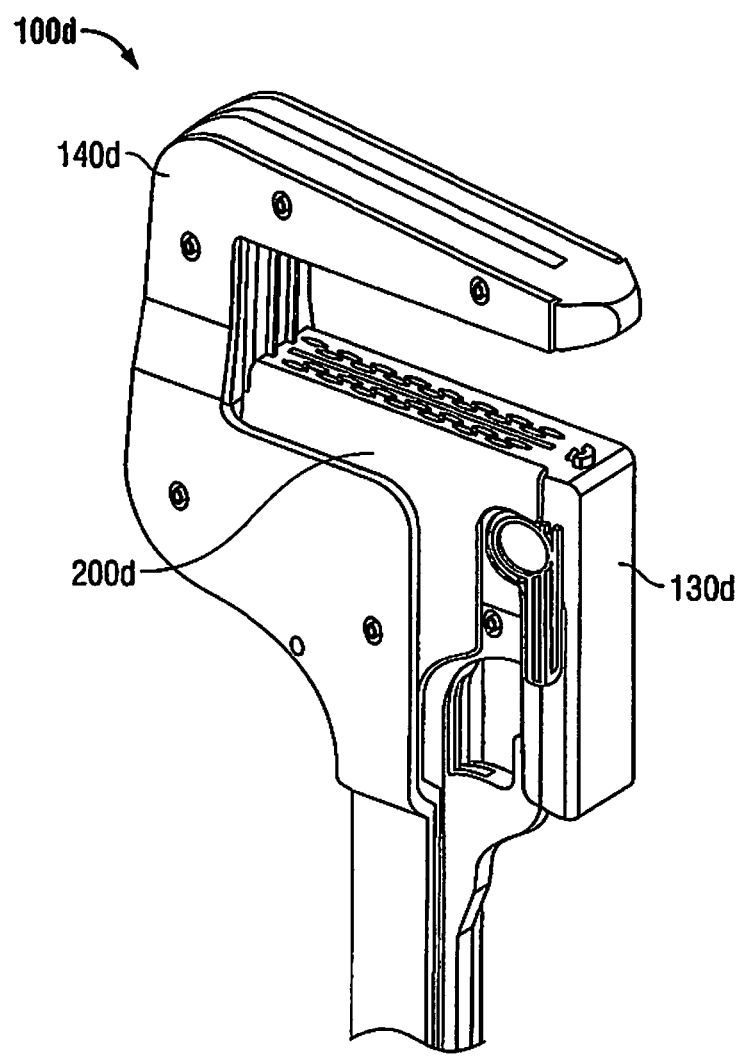
FIG. 7 illustrates an alternate embodiment of the stapling instrument and showing a perspective view of the distal end portion of the instrument with the guide pin, clamp and cartridge in a proximal position.

To return clamp 200c to its original position, it is envisioned that the clamp handle is at least partially retracted towards its original position, thus causing proximal translation of the elongated member, which causes proximal translation of clamp 200c. To return the jaw members to their original position, it is envisioned that the firing handle is at least partially retracted towards its original position, thus causing proximal translation of the second elongated member, which causes proximal translation of cartridge assembly 130c with respect to anvil assembly 140c, for example. In some embodiments, a spring can be provided to bias the elongated members, jaw members or handle(s) to the retracted position In the illustrated embodiment of FIG. 3, cartridge assembly 130c includes two rows of (staggered) staples (staple pockets 302c are shown in FIG. 3) and knife 220c (as evidenced by knife channel 221c). The knife channel 221c (and knife 220c) is positioned adjacent only one of the rows of staples as shown. The two rows of staples help reduce the profile of the end effector and may also help provide better detection of margins (the outer limits of the stapled organ). It is also envisioned that one row of staples or more than two rows of staples can be used, e.g., two pairs of two rows of staples—one pair on each side of knife 220c (as shown in FIG. 7). Also, the number of rows on each side of the knife need not be equal. For example, one row of staples can be provided on one side of the knife and two rows of staples provided on the other side of the knife.

Figure 8:
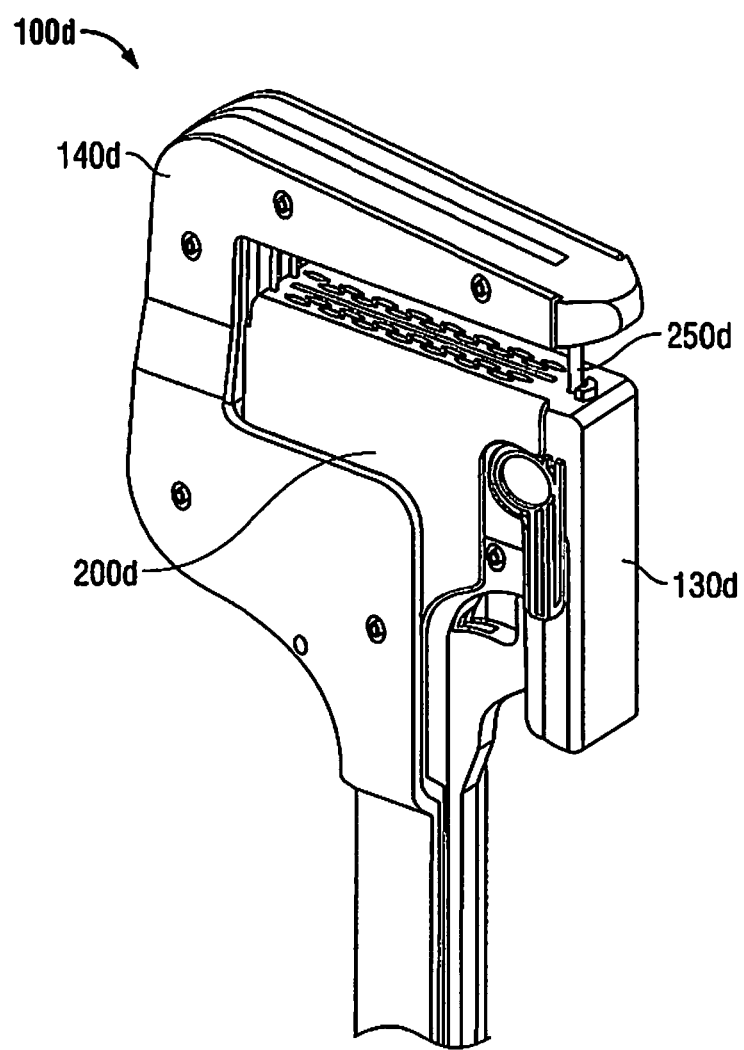
FIG. 8 is a perspective view similar to FIG. 7 showing the guide pin in a distal position.
Figure 9:
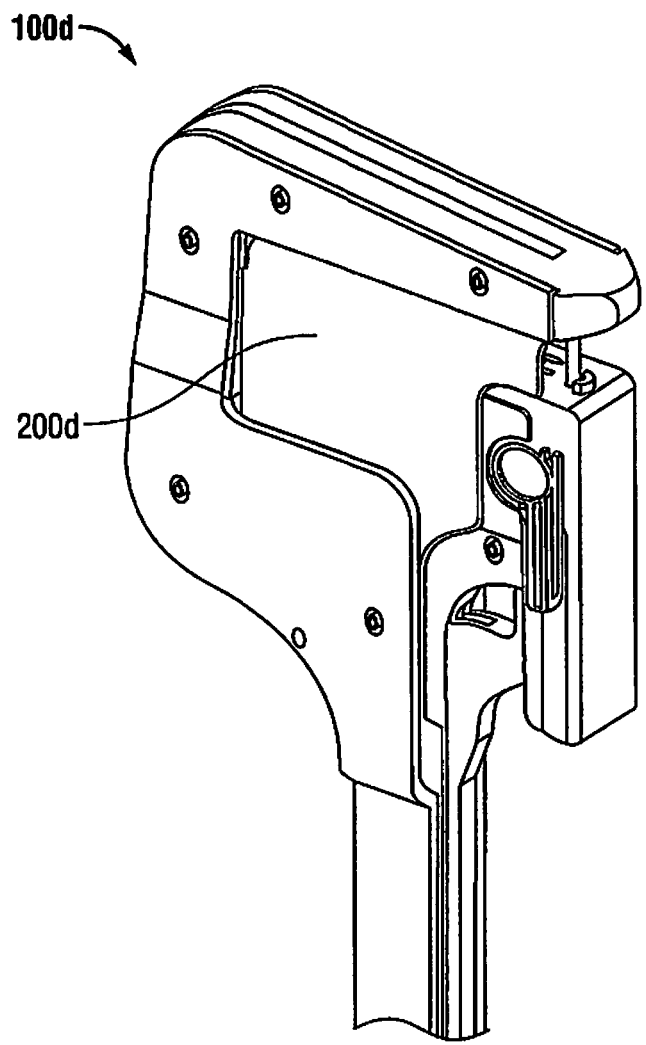
FIG. 9 is a view similar to FIG. 7 showing the guide pin and clamp in a distal position.
Figure 10:
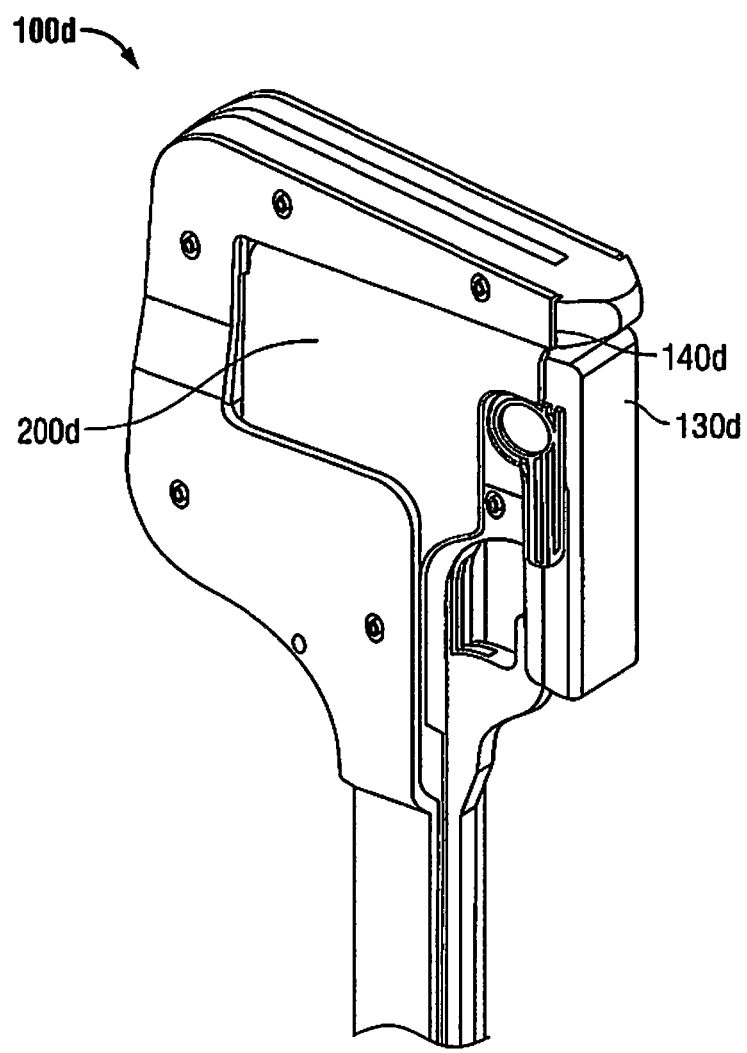
FIG. 10 is a view similar to FIG. 7 showing the guide pin, clamp and cartridge in a distal position.
Figure 11:
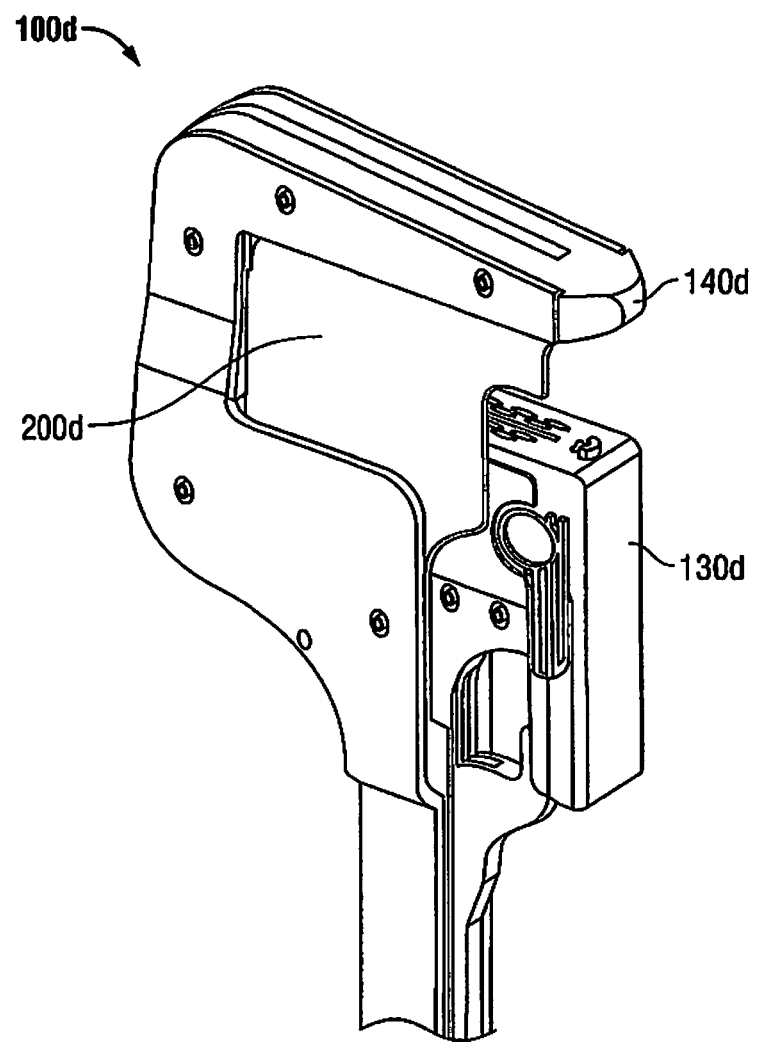
FIG. 11 is a view similar to FIG. 7 showing the guide pin and cartridge in the proximal position and the clamp in the distal position.
Figure 12:
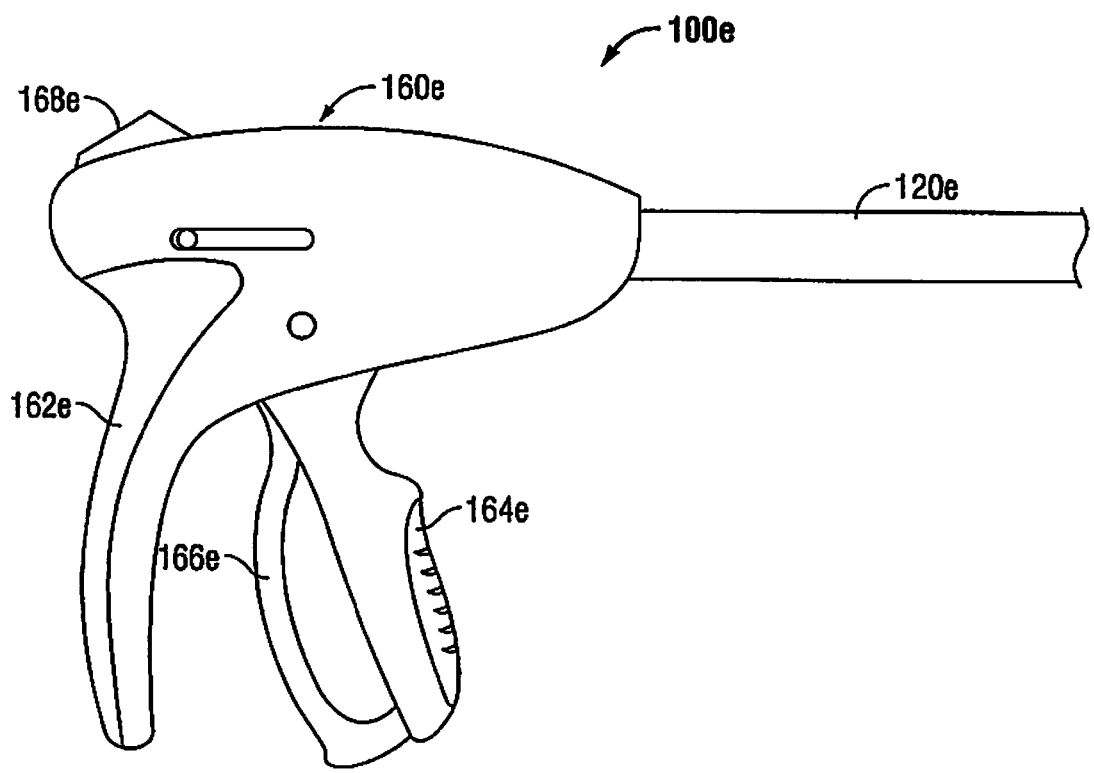

With reference to FIGS. 7-11, another embodiment of the distal portion of the surgical stapling instrument 100d is shown, utilizing the cartridge assembly of FIGS. 1 and 2B. The steps of using surgical stapling instrument 100d of this embodiment will be described (with the tissue, e.g. organ, being omitted for clarity). FIG. 7 shows the end effector positioned such that the organ or other tissue to be stapled is situated between cartridge assembly 130d and anvil assembly 140d. Next, FIG. 8 illustrates the advancement of guide pin 250d. Clamp 200d is then translated distally to compress the tissue against a portion of the anvil assembly 140d (which may temporarily occlude the organ), as shown in FIG. 9. Next, with reference to FIG. 10, the jaw members are approximated to clamp tissue therebetween by advancing the cartridge assembly 130d towards the anvil assembly 140d. (It is also contemplated that in alternate embodiments, the anvil assembly can be moved toward the cartridge assembly to clamp tissue or both the cartridge and anvil assemblies can be movable toward each other to clamp tissue). Staples are then fired from cartridge assembly 130d toward anvil pockets (a few representatively shown in FIG. 4 designated by reference numeral 142c; not explicitly shown in FIGS. 7-11) of anvil assembly 140d where they are deformed by the anvil pockets. Knife (evidenced by knife channel 221d in FIG. 11) is translated distally from cartridge assembly 130d through tissue either during, e.g. along with the firing of the staples, or following the firing of staples. After firing the staples, guide pin 250d and cartridge assembly 130d are retracted proximally as shown in FIG. 11. Retraction can occur either, simultaneously or consecutively (sequentially). Clamp 200d is also retracted proximally, such that surgical stapling instrument 100d can be removed from the organ.

Figure 13:
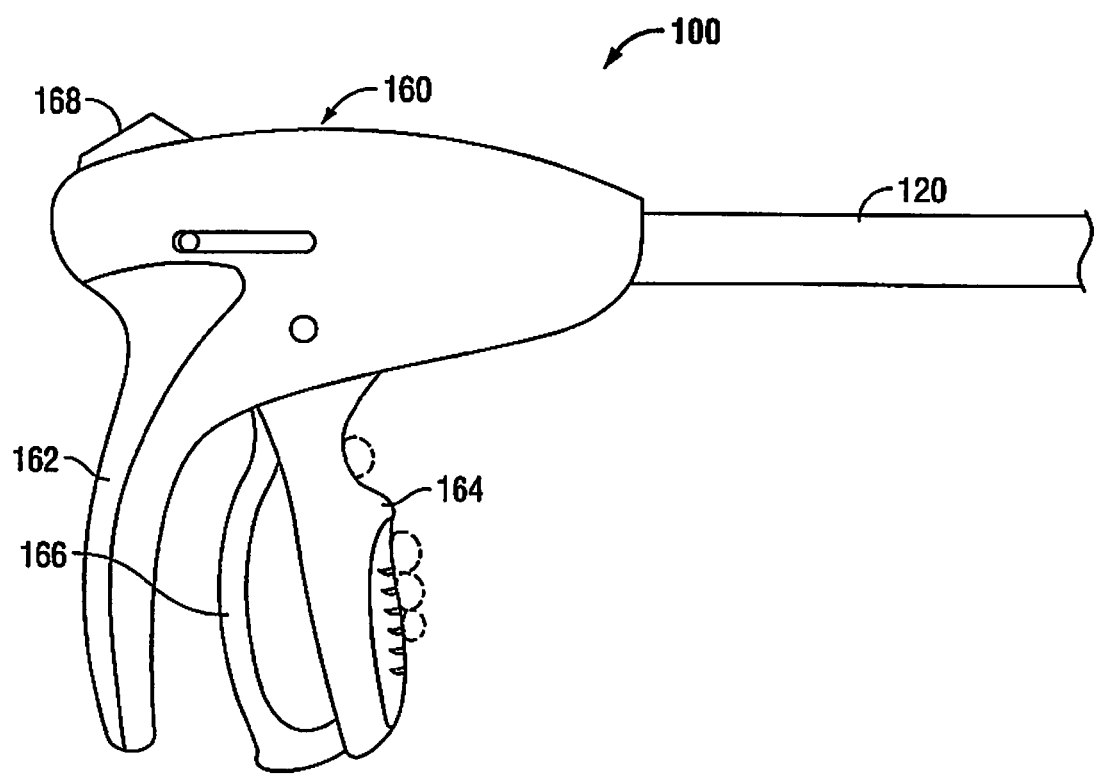
Figure 14:
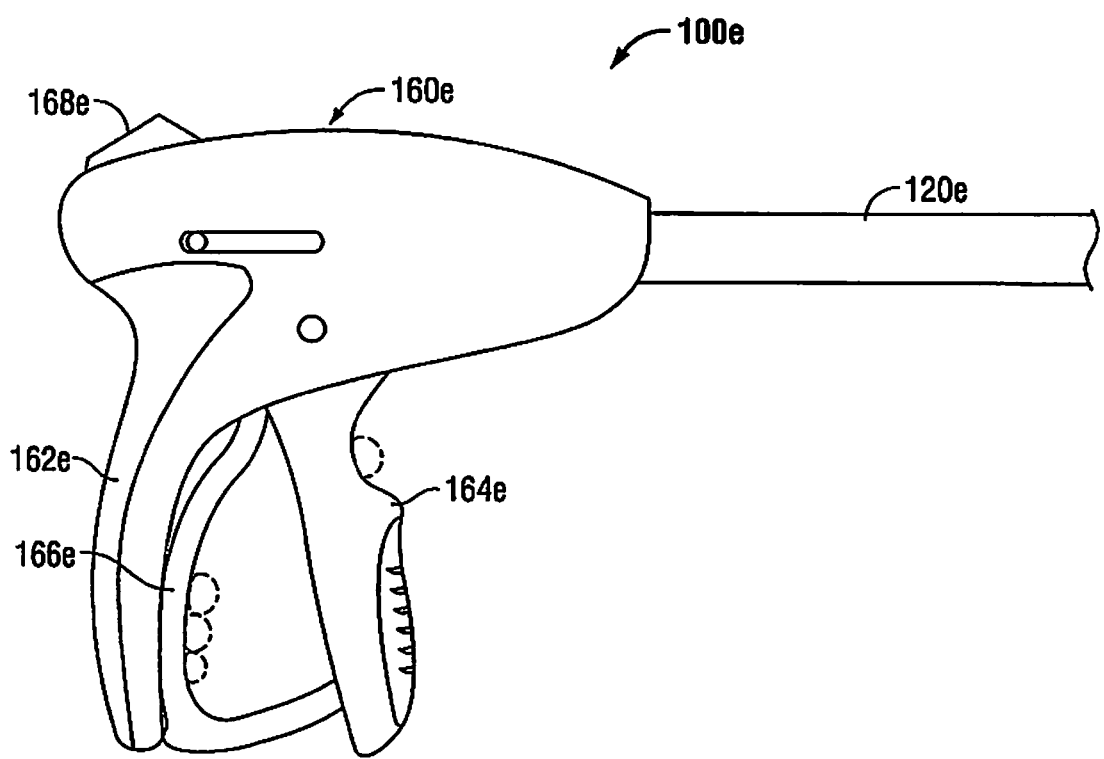

The various actuations of surgical stapling instrument 100 to clamp, approximate the cartridge, and fire the staples can be achieved by myriad techniques. For example, in one embodiment shown in FIGS. 12-15, handle portion 160e of surgical stapling instrument 100e is shown in various stages of actuation. Handle portion 160e includes a stationary handle 162e, a first movable handle 164e, a second movable handle 166e (e.g., sharing a common pivot point with first movable handle 164e) and a release button 168e. In this embodiment, it is envisioned that a partial actuation of first movable handle 164e (towards stationary handle 162e), as shown in FIG. 13, causes the clamp to advance distally as the mechanism for advancing the clamp is operatively connected to first movable handle 164e. For example, an elongated member (not shown) from which the clamping head extends is slidably positioned within the elongated portion 120e and is connected to an upper portion of movable handle 164e via a pin (not shown). In this manner, when handle 164e is pulled proximally, it forces the elongated member distally to advance the clamp.

Figure 15:
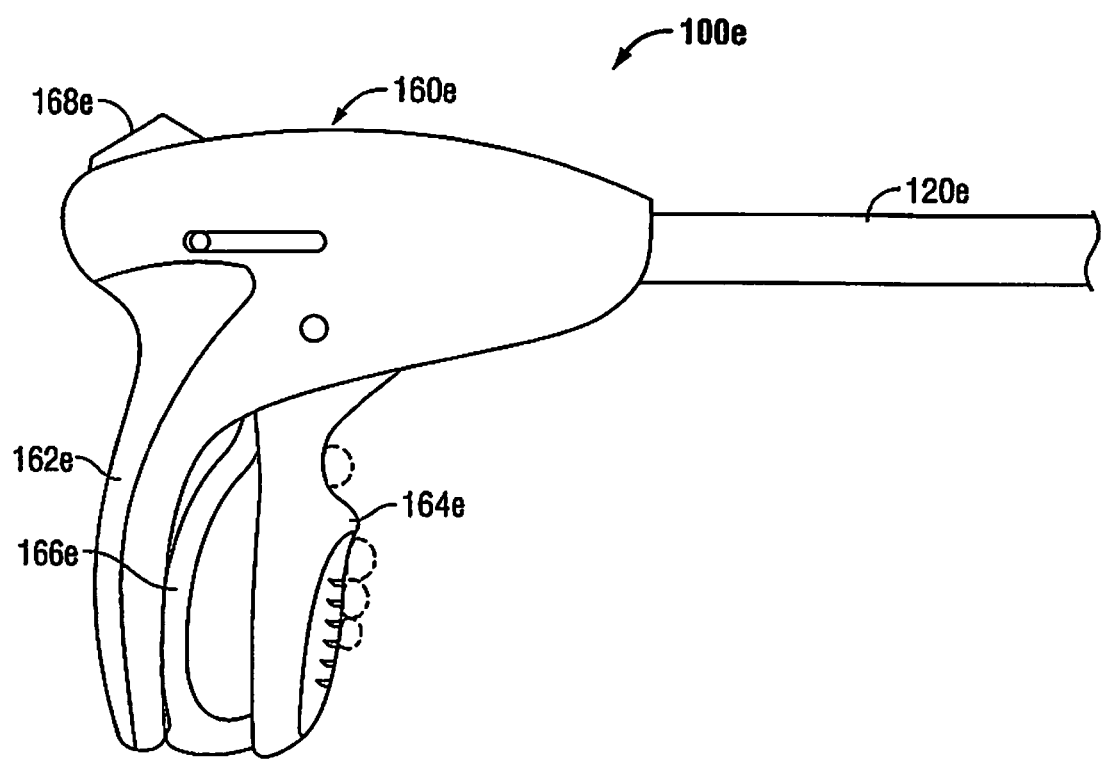

After pivoting of first movable handle 164e, second movable handle 166e is actuated. Actuation of second movable handle 166e (e.g., towards stationary handle 162e) (see FIG. 14) causes the guide pin(s) to translate distally and causes approximation of the jaw members as the mechanism for advancing the guide pin(s) and at least one jaw member (e.g., cartridge assembly) is operatively connected to second movable handle 166e via, for example, an elongated member attached by a pin to the upper portion of the handle 166e. Consequently, in this example, when movable handle 166e is pivoted rearwardly, it pivots an attached linking member which is connected to a proximal end of a pin advancement member as well as advances an elongated approximation bar which engages the cartridge to slide it distally. Subsequently, first movable handle 164e can be further actuated as shown in FIG. 15 to advance a firing bar within elongated portion 120e to contact staple pushers contained in the cartridge assembly to engage and advance the staples distally from the cartridge assembly toward the anvil assembly. Thus, a single handle can be utilized to approximate the jaws and fire the fasteners in the manner described in U.S. Pat. No. 6,817,508, the entire contents of which are incorporated herein by reference.

It is further envisioned that release button 168e can be actuated to release the clamp (e.g., from a locked position) such that the clamp retracts proximally. Here, it is envisioned that release button 168e is disposed in mechanical cooperation with the mechanism for advancing the clamp, such that depression of release button 168e unlocks the mechanism for advancing the clamp from an actuated (e.g., distal) position. Such release button can be similar to the release button of U.S. Pat. No. 6,817,508 to release the jaws.

It is also envisioned in an alternate embodiment that actuation of second movable handle 166e simultaneously causes distal translation of clamp 200 and approximation of the jaw members. In such an embodiment, both the mechanism for advancing the clamp and the mechanism for advancing at least one jaw member are in mechanical cooperation with second movable handle 166e. For example, an actuator within body 160e would first advance a clamping bar attached to the clamp and after full advancement of the clamp would engage an approximation bar for advancing the cartridge.

While not explicitly shown in the illustrated embodiments, it is also envisioned that second movable handle 166e is movable towards and/or into engagement with first movable handle 164e, e.g., to distally translate the clamp. It is further envisioned that a partial actuation of first movable handle 164e causes the guide pin(s) to translate distally and/or to cause approximation of the jaw members. Additionally, a continued actuation of first movable handle 164e may cause staples to be fired as a proximal portion of a firing rod is mechanically engaged with first movable handle 164e and a distal portion of the firing rod is mechanically engaged with pushers of the cartridge assembly.

Further, it is also contemplated that the first movable handle 164e is physically prevented (e.g., via a lockout in handle portion 160e) from being actuated until second movable handle 166e has been actuated and is engaged therewith. In this embodiment, the jaw members cannot be approximated and staples cannot be fired until the clamp has been actuated to compress tissue.

Other methods of actuating the surgical stapling instrument 100, including a method for performing a lower anterior resection ("LAR"), are also envisioned. For instance, the handle portion may include a single movable handle that may be squeezed multiple times, where each actuation can perform a distinct operation. That is, a first actuation of the movable handle may actuate clamp 200, a second actuation of the movable handle may approximate the jaw members, and a third actuation of the same movable handle may deploy staples and knife.

Figure 16:
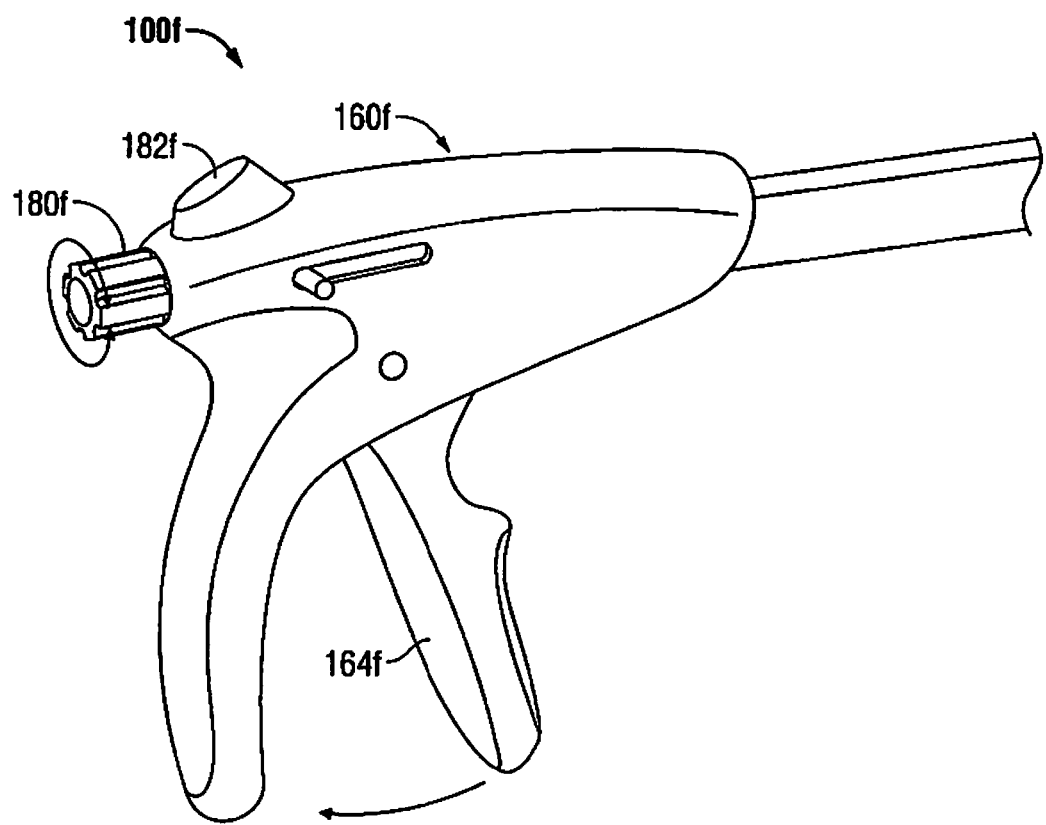
FIGS. 16-18 illustrate alternate embodiments of handle portions of the surgical stapling instrument according to the present disclosure.

Another method of actuation of surgical stapling instrument 100f is illustrated in FIG. 16. Here, a first actuation (or partial actuation) of movable handle 164f advances the clamp, as the mechanism for advancing the clamp, e.g. an elongated bar from which the clamp head extends, is mechanically engaged with an upper portion of movable handle 164f via a pin within the handle portion, for example. Next, the turning of a knob or screw 180f in a first direction approximates the jaw members, as knob 180f is in mechanical cooperation with a threaded elongated rod such that rotation of knob 180f in one direction causes the elongated rod to longitudinally translate (distally) to advance the cartridge jaw member and reverse rotation retracts the cartridge jaw member. A second actuation of movable handle 164f then fires staples and/or advances the knife. The user can then press a release button 182f to open the jaw members as in the aforementioned U.S. Pat. No. 6,817,508. Here, for example, button 182f is in mechanical cooperation with a lockout mechanism that maintains the jaw members in an approximated position. Activation of button 182f mechanically disengages the lockout mechanism, thus causing or enabling the jaw members to open. Additionally, a user may then turn knob 180f in a second direction to translate the elongated rod (e.g., proximally) to cause the jaw member to return to its original position.

In an alternate embodiment, a rotational knob or screw can be used to advance the clamp and another rotational screw used to approximate the jaw members. In another alternate embodiment, a rotational knob or screw can be used to advance the clamp and a pivotable handle used to approximate the jaw members.

Figure 17:
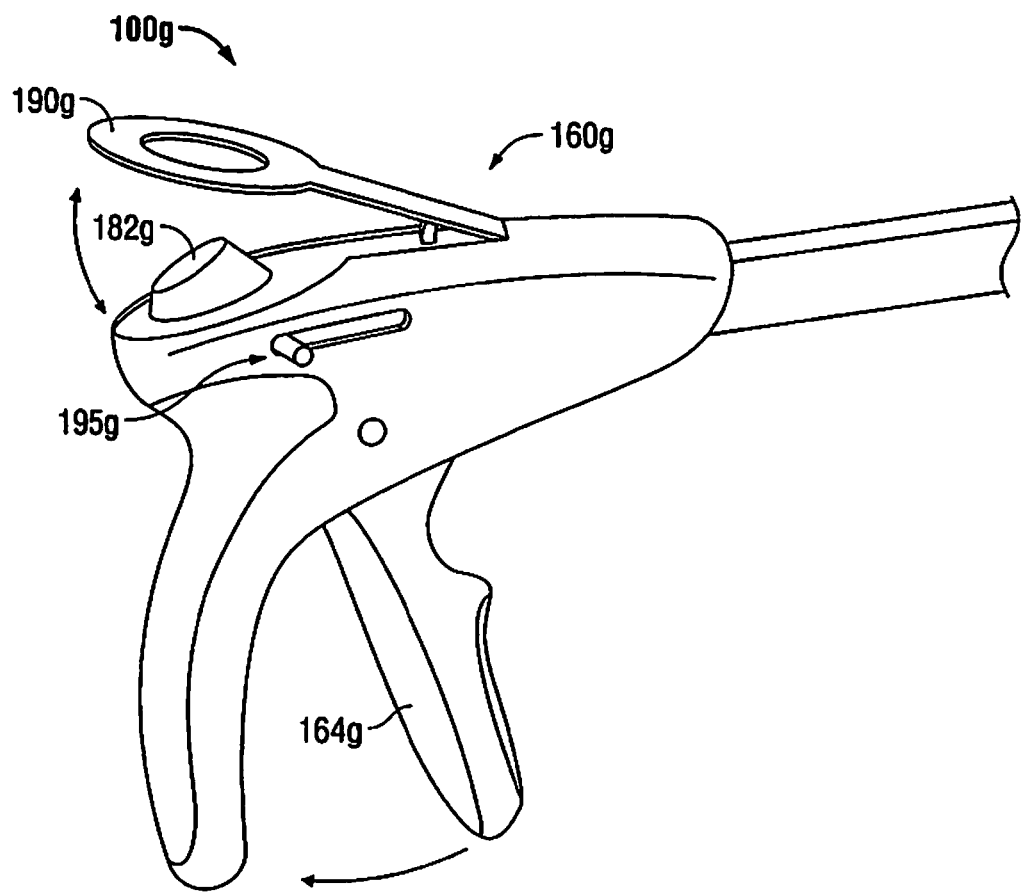

FIG. 17 illustrates another embodiment of handle portion 160g of surgical stapling instrument 100g. Here, the clamp is actuated by closing a lever 190 (illustrated in the open position) which pivots with respect to handle portion 160g. Such pivoting motion is translated to axial motion via a pivoting linkage member, for example, which connects the lever to an elongated member which has a clamping member positioned at a distal end portion After advancement of the clamp, the jaw members are approximated by actuation (or partial actuation) of movable handle 164g. (Alternatively, a rotational knob can be utilized to approximate the jaw members). A second actuation (or continued actuation) of movable handle 164g causes staples to be fired and the knife to be advanced. To open the jaw members, the user can press release button 182g. Here, for example, button 182g is in mechanical cooperation with a lockout mechanism that maintains the jaw members in an approximated position. Activation of button 182g mechanically disengages the lockout mechanism, thus causing or enabling the jaw members to open. Additionally, moving lever 190g to its original position pivots the linkage in the other direction to return clamp proximally towards its original position, e.g., by causing the elongated member to translate proximally.

Figure 18:
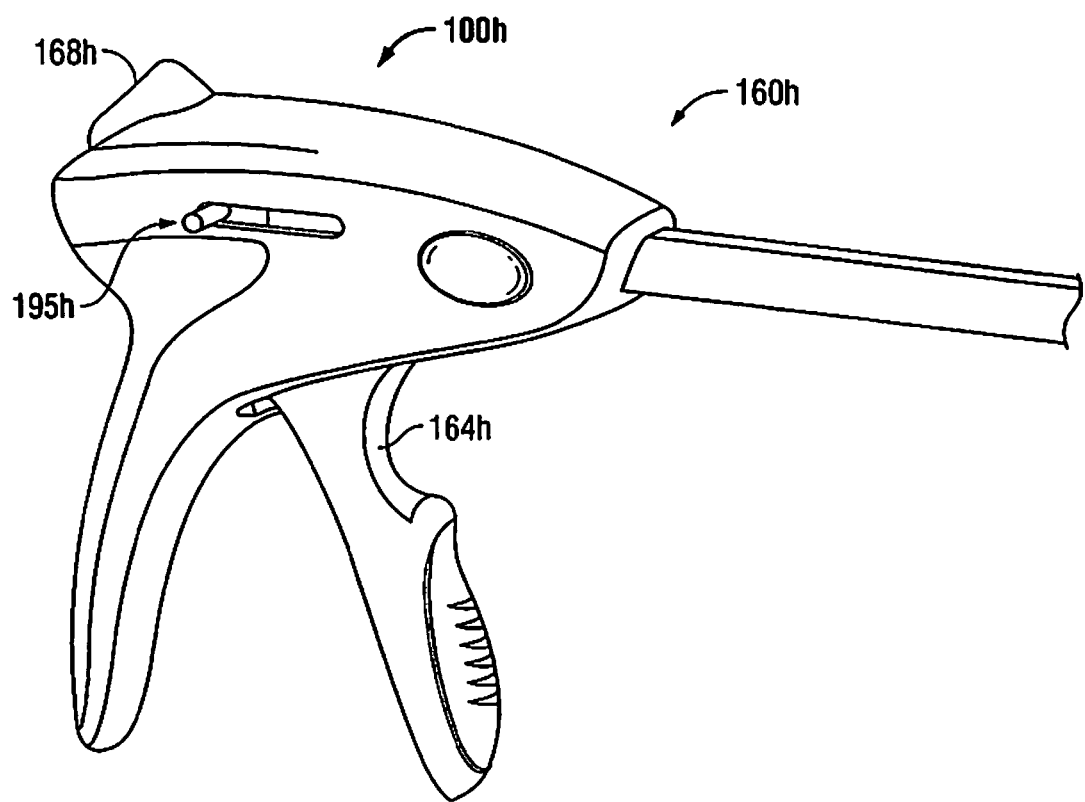

Another alternate embodiment of handle portion 160h of surgical instrument 100h is illustrated in FIG. 18. Here, handle portion 160h includes a single movable handle 164h and a release button 168h. In this embodiment, it is envisioned that a first actuation of movable handle 164h distally translates an elongated member to translate the clamp to compress tissue. A second actuation of movable handle 164h distally translates a closure member, which causes at least one jaw member to move towards the other jaw member to grasp tissue therebetween. A third actuation of movable handle 164h distally translates a firing rod, which causes staples to be fired from the cartridge assembly. Additionally, release button 168h may be disposed in mechanical cooperation with at least one of the elongated rod and the closure rod such that pressing release button 168h causes a lockout mechanism (disposed within handle portion 160h) to release the clamp and/or the jaw members from a locked approximated position.

It is further envisioned that guide pin(s), of the various embodiments, can be independently advanced by a structure 195g, 195h (e.g., a slide) disposed on or adjacent handle portion 160h (see FIGS. 17 and 18, for example). Additionally, any combination of the disclosed features including the first movable handle, second movable handle, knob, clamp handle, slide an button may be used to advance guide pin(s), advance clamp, approximate the jaw members, fire staples, transect tissue, open the jaw members, proximally translate clamp, and proximally translate guide pin(s).

Figure 19:
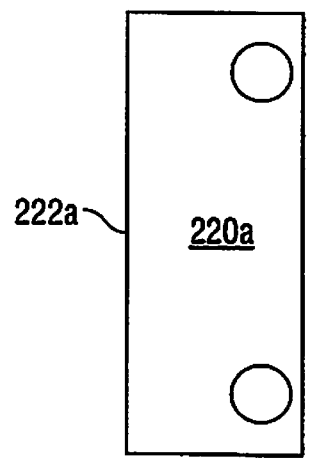
FIGS. 19-21 illustrate various configurations of a knife of the surgical stapling instrument according to various embodiments of the present disclosure.
Figure 20:
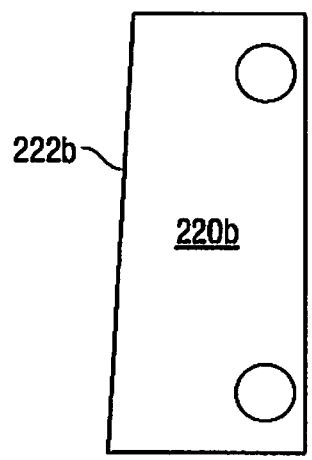
Figure 21:
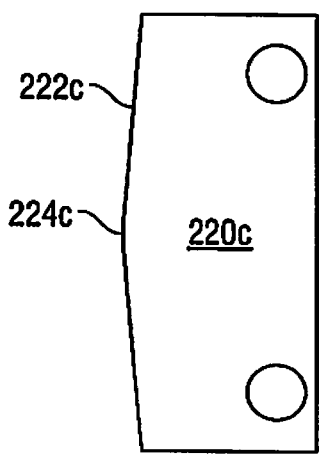

Various embodiments of different knife blades 220 are shown in FIGS. 19-21. Specifically, FIG. 19 illustrates knife blade 220a having a tissue-contacting surface 222a that is substantially parallel to the tissue-contacting surface of cartridge assembly 130. In this embodiment, all parts of the tissue, e.g. organ, would be transected substantially simultaneously. In the embodiment shown in FIG. 20, knife blade 220b includes a longitudinally tapered tissue-contacting surface 222b (e.g. guillotine-like). Here, as can be appreciated, the parts of the tissue, e.g. organ, would be transected sequentially. That is, either the proximal portion of the organ will be transected prior to transaction of the distal portion of the organ, or vice versa, depending on the orientation of knife blade 220b with respect to cartridge assembly 130. A third embodiment of knife blade 220c is illustrated in FIG. 21. In this configuration, tissue-contacting surface 222c of knife blade 220c is elevated or raised near its center, with respect to the sides—i.e., a point 224c is formed. Here, knife blade 220c initially cuts the tissue, e.g. organ, from the center of contact, and subsequently cuts portions of the organ disposed distally and proximally of the center. As can be appreciated, a lower amount of firing force may be necessary for a complete transection using the knife configurations of FIGS. 20 and 21.

It is further envisioned that surgical stapling instrument 100 of the present disclosure does not include a knife 220. Rather, after the organ has been stapled, the surgeon can use another instrument to transect the tissue.

Figure 22:
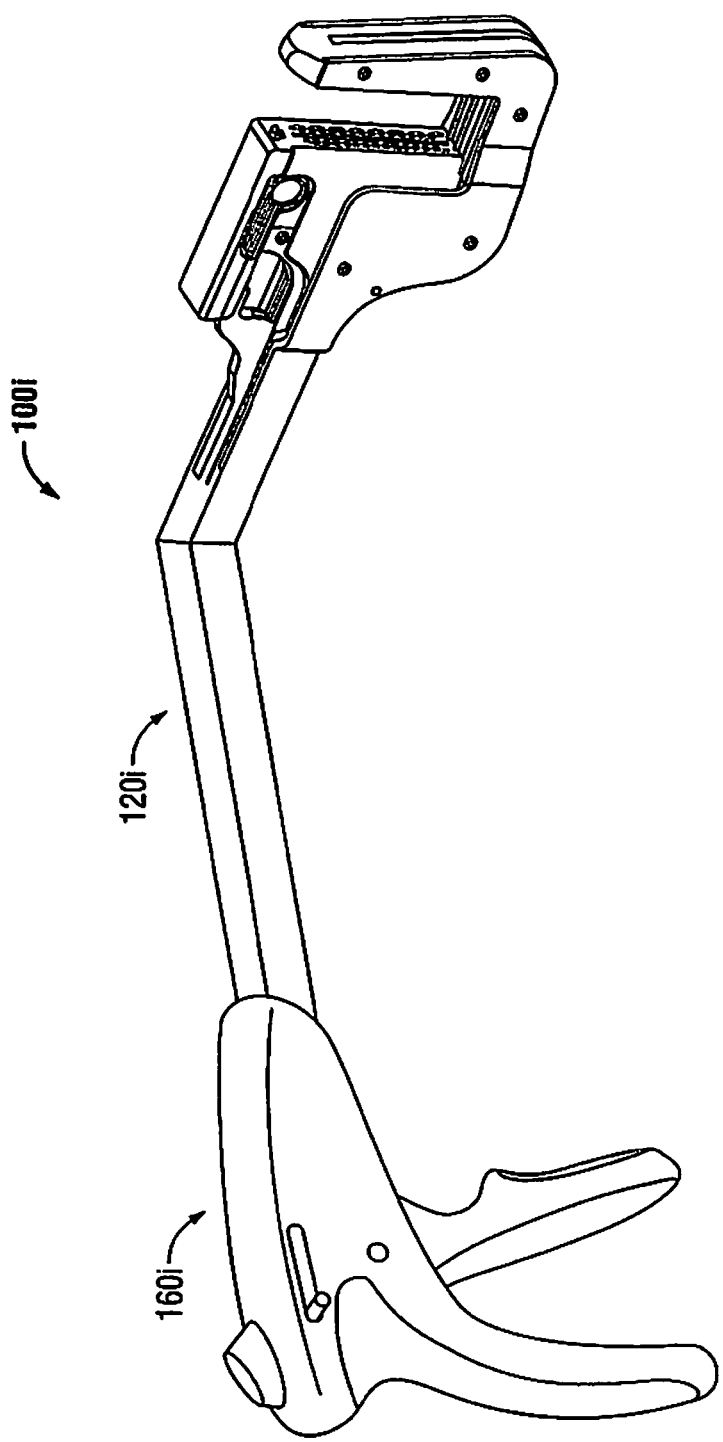
FIG. 22 illustrates an alternate embodiment of the surgical stapling instrument of the present disclosure including an elongated portion having a bend.

It is contemplated that the elongated portion 120, 120i of surgical stapling instrument 100, 100i, can be curved (e.g., gradually curved as in FIG. 1) and/or bent (e.g., includes a sharp corner or angle as in FIG. 22) and/or twisted to facilitate access and/or visualization (e.g., into a patient's pelvic cavity) or straight. With specific regard to surgical stapling instrument 100 of FIG. 1, the radius of curvature of the curve can be different from the amount of curvature shown. Additionally, the apex of the curve could be located farther distally or proximally than what is shown. With specific regard to surgical stapling instrument 100i of FIG. 22, it is envisioned that the angle of the bend can be more acute or obtuse than the angle shown. Further, the location of the bend can be closer to or further from handle portion 160i than what is illustrated. In an alternate embodiment, the elongated portion can include a twist. In other embodiments, the elongated portion can be straight.

In yet additionally envisioned embodiments, cartridge assembly, anvil assembly, knife, and/or staple pusher(s) may be disposable. An example of such a configuration is shown in commonly-owned, U.S. Pat. No. 4,383,634 to Green, the entire contents of which are hereby incorporated by reference herein. Further, surgical stapling instruments of the present disclosure may include a multiple pusher configuration or a single pusher configuration.

The present disclosure also includes a method of using the surgical stapling instruments described above. The method includes the steps of providing a surgical stapling instrument, using the surgical stapling instrument to clamp tissue, approximate its jaw members, and fire staples (fasteners). The method may also include the steps of advancing a guide pin, transecting tissue, opening the jaw members, releasing the guide pin and releasing the clamp from the tissue.

The present disclosure also relates to a method of using the described surgical instrument. The method, as described above, includes providing a surgical instrument, clamping tissue via the clamp, approximating the jaw members, firing staples (e.g., simultaneously), and/or cutting tissue (e.g., with a knife disposed in mechanical cooperation with the surgical instrument, or using a separate instrument). In certain embodiments, the instrument is used for lower anterior resection. First, the clamp is actuated, clamping onto intestinal tissue. Then, the interior of the intestinal tissue is washed out or otherwise cleansed. The tissue is then cut and stapled. In this way, the interior intestinal tissue is cleansed up to the location of the clamp, including the area where the jaws will engage the intestinal tissue to be stapled and/or cut, once the jaws are approximated.

Additionally, it is envisioned that the cartridge assembly includes more than two rows of staples. Additionally, while the knife is located at various positions in the illustrated features, the present disclosure includes embodiments where the location of the knife with respect to the cartridge assembly is in other locations.

The present disclosure also relates to a loading unit configured for releasable engagement with a surgical instrument. The loading unit includes a pair of jaw members and a clamp, and is configured for releasable engagement with a distal portion of the elongated portion of the surgical instrument. The loading unit can also include a knife. At least one of the jaw members is movable with respect to the other between an open position and an approximated position for engaging body tissue therebetween. The clamp is movable between an open position and an approximated position for engaging body tissue. The loading unit mechanically cooperates with a corresponding mechanisms of the surgical instrument to close the clamp and approximate the jaw members.

Although the clamp is described above as being part of the instrument, it is also contemplated that the clamp is a separate component attachable to the instrument. The clamp would attach to the part of the instrument, such as the instrument shaft, and include a mechanism for sliding the clamp distally. In such embodiments of separate clamps, the clamp could be packaged with the instrument or could be packaged separately.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the disclosure.

The invention claimed is:
1. A surgical instrument comprising:
   a handle portion;

an elongated portion extending distally from the handle portion and having a longitudinal axis;

a pair of jaw members disposed adjacent a distal end of the elongated portion, at least one of the jaw members being movable with respect to the other jaw member in a distal direction between an open position and an approximated position for engaging body tissue therebetween, one of the jaw members includes a plurality of rows of fasteners positioned substantially transverse to a longitudinal axis of the elongated portion and arranged in substantially linear rows, and a tissue-contacting surface of each of the jaw members is disposed substantially transverse to the longitudinal axis of the elongated portion; and a clamp having a clamping surface extending substantially transversely from an elongated member, the elongated member being parallel to the longitudinal axis, and having a height exceeding the height of the elongated member to extend adjacent the jaw containing the plurality of fasteners, the clamp being movable in a direction that is parallel to the elongated portion from a proximal position to a distal position relative to the movable jaw member for engaging body tissue.

2. The surgical instrument of claim 1, wherein the clamp is independently movable in a distal direction with respect to the jaw members.

3. The surgical instrument of claim 1, wherein the clamp moves automatically with approximation of the jaw members.

4. The surgical instrument of claim 1, further including a knife movable from a proximal to a distal position, the knife including a longitudinally tapered tissue-contacting surface.

5. The surgical instrument of claim 1, further including a knife movable from a proximal to a distal position, the knife including a tissue-contacting surface having a raised middle portion with respect to its side portions.

6. The surgical instrument of claim 1, wherein the handle portion includes a first mechanism to distally advance the clamp and a second mechanism to approximate the jaw members.

7. The surgical instrument of claim 1, wherein the elongated portion includes at least one of a curved portion and a bend.

8. The surgical stapling instrument of claim 1, wherein at least one of the jaw members is configured to be removable from the instrument.

9. The surgical instrument of claim 1, wherein the jaw containing the fasteners includes two rows of staples and a knife disposed between the two rows of staples, and the other jaw has a plurality of pockets to form the staples.

10. The surgical instrument of claim 1, wherein the jaw containing the fasteners includes first and second rows of staples and a knife, wherein one of the rows of staples is disposed between another of the rows of staples and the knife, and the other jaw has a plurality of pockets to form the staples.

11. The surgical stapling instrument of claim 1, wherein the height of the clamping surface of the clamp is greater than a length of a knife slot which accommodates a knife.

12. The surgical instrument of claim 1, wherein the clamp is disposed externally of the movable jaw member.

13. The surgical instrument of claim 1, wherein one of the jaw members is a fixed jaw member that is fixed from movement with respect to the elongated portion, and wherein the clamp is distally translatable toward the fixed jaw member.

14. The surgical instrument of claim 1, wherein a distal portion of the clamp is movable distally beyond a distal-most portion of the movable jaw member.

15. The surgical instrument of claim 1, wherein the handle portion includes a first actuation mechanism configured to distally advance the clamp and a second actuation mechanism configured to distally advance the movable jaw member.

16. The surgical instrument of claim 1, wherein the height of the clamping surface of the clamp exceeds the height of at least one of the jaw members.

17. The surgical instrument of claim 1, wherein the height of the clamping surface of the clamp exceeds the height of the jaw member containing the plurality of fasteners.

18. The surgical instrument of claim 1, wherein the clamp is fixed from moving toward the longitudinal axis.

19. The surgical instrument of claim 1, wherein the jaw members are relatively movable into the approximated position prior to distal movement of the clamp.

20. The surgical instrument of claim 1, wherein the fasteners are ejectable from one of the jaw members prior to distal movement of the clamp.

* * * * *